(12) United States Patent
Colpan

(10) Patent No.: US 6,274,371 B1
(45) Date of Patent: Aug. 14, 2001

(54) PROCESS AND DEVICE FOR THE ISOLATION OF CELL COMPONENTS, SUCH AS NUCLEIC ACIDS, FROM NATURAL SOURCES

(75) Inventor: Metin Colpan, Essen (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 08/809,072

(22) PCT Filed: Feb. 3, 1995

(86) PCT No.: PCT/EP95/00392

§ 371 Date: Jun. 19, 1997

§ 102(e) Date: Jun. 19, 1997

(87) PCT Pub. No.: WO96/08500

PCT Pub. Date: Mar. 21, 1996

(30) Foreign Application Priority Data

Sep. 14, 1994 (DE) ................................................. 44 32 654

(51) Int. Cl.[7] .............................. C12M 1/33; C12N 1/06; G01N 33/53
(52) U.S. Cl. ........................ 435/259; 435/306.1; 435/975
(58) Field of Search ..................................... 435/259, 287, 435/306.1, 975

(56) References Cited

U.S. PATENT DOCUMENTS

| 4,923,978 | 5/1990 | McCormick | 536/27 |
| 5,004,806 | 4/1991 | Kung | 530/415 |
| 5,057,426 | * 10/1991 | Henco et al. | 435/270 |

FOREIGN PATENT DOCUMENTS

| 0268946 | 6/1988 | (EP) . |
| 0442026 | 8/1991 | (EP) . |

\* cited by examiner

*Primary Examiner*—Deborah K. Ware
(74) *Attorney, Agent, or Firm*—Jacobson Holman, PLLC

(57) ABSTRACT

A filtration process for the preparation of nucleic acids from natural sources is disclosed. The sources containing nucleic acids are lysed; the lysate is left to rest for some time; the resulting lysate passes a filter layer. The filter layer is selected from silica gel, aluminum oxide or packed diatomaceous earth, or interwoven or cemented non-wovens of glass fibers and silica gel. Other filter layers include cellulose, paper, compressed paper, and paper non-wovens. The fraction leaving the filter layer is then collected and the nucleic acid is subsequently isolated and purified from the collected fraction. Furthermore, the filter layer has not been modified with anion exchange groups.

15 Claims, 1 Drawing Sheet

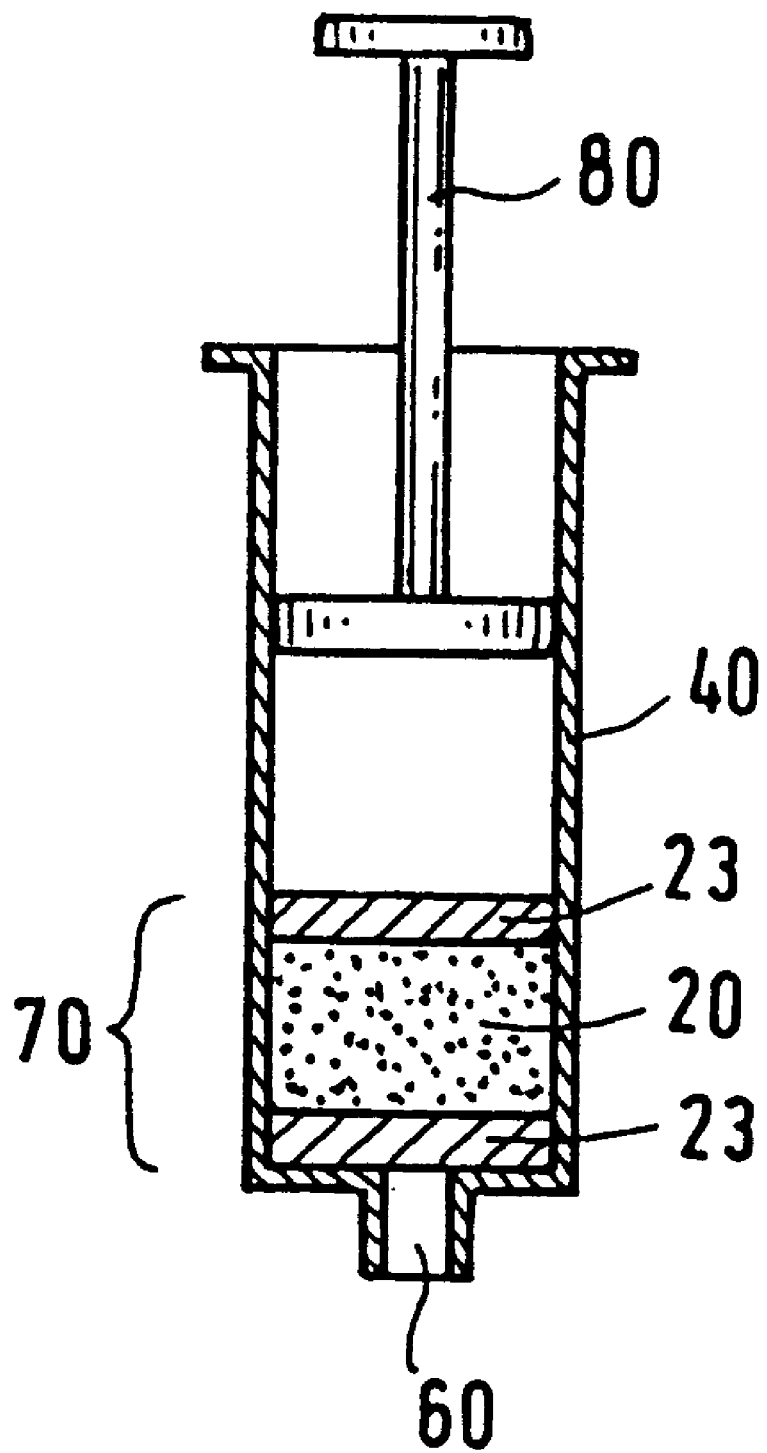

PROCESS AND DEVICE FOR THE ISOLATION OF CELL COMPONENTS, SUCH AS NUCLEIC ACIDS, FROM NATURAL SOURCES

This application is a 371 of PCT/EP95/00392 filed Feb. 3, 1995.

This invention is directed to a process for the preparation of nucleic acids from natural sources, such as *E. coli* cells, human and animal cells, by separating the lysed natural sources, such as cells or cell debris, in a sample by filtration, and to a kit containing means for performing said process.

Frequently, in the preparation of cell components, particularly nucleic acids, the problem arises to separate the lysed natural sources, from which the components are derived, from dissolved material. Usually, the separation of cells or cell debris is effected by centrifugation, whereby cell fragments or cells deposit as a pellet in the centrifuge tube. The dissolved cell components then are found in the supernatant and may be pipetted. In the preparation of nucleic acids, simple filtration methods were not successful for the separation of the lysed cells or their fragments because the cell fragments either pass through the filter having too large a pore size and thus give rise to turbidity and impurities in the filtrate or, when filters with appropriately narrow pores are used, inevitable jamming will result, so that a purposeful preparation of the cell components is no longer possible.

Thus, the present invention is based on the problem of providing a process and creating a device by means of which centrifugation steps for the preparation of cell components from natural sources, such as cells, may be avoided by using filtration steps which are easier to handle.

Conventionally, in order to isolate components from cells, the latter are lysed first. In the preparation of nucleic acids, the cells have to be lysed first, for instance, by using enzymes, such as e.g. proteinase K and lysozyme, detergents, such as SDS, Brij, Triton X 100, Tween 10, and DOC, and chemicals, such as sodium hydroxide, guanidine hydrochloride and guanidine isothiocyanate. The cell fragments are sedimented by centrifugation, and the supernatant is decanted or pipetted off and subsequently purified by chromatography or extraction with phenol or chloroform and an alcohol precipitation. Maniatis; Current Protocols in Molecular Biology, Ausubel, F. M. et al., eds. (1991), Wiley Interscience, New York; Birnboim H. C. and Doly, J. (1979), A Rapid Alkaline Extraction Procedure for Screening Recombinant Plasmid DNA. Nucl. Acids Res. 7, pp 1513–1522.

Such centrifugation in a conventional laboratory centrifuge, e.g., Heraeus Biofuge GL, Beckmann GS6, will take from 15 min to 2 h at from 3,000 rpm to 20,000 rpm, depending on the particular application and the particle size of the cell fragments. This means that with large sample numbers, the centrifugation will require much personnel and involve losses in time. Therefore, it is desirable to be provided with a simple and rapid process for the removal of the cell fragments.

In preliminary experiments, the filter materials and filtration methods which have been available to date have proven to be unsuited for the separation of such biological cell debris. Sterile filters, e.g. made of nylon or cellulose acetate, having pore sizes of from 0.2 $\mu$m or 0.45 $\mu$m will instantly clog and lack the capacity of retaining a larger amount of cell fragments.

These filters are only useful for the filtration of liquids having a very low content of solids or cellular contaminations.

In the filtration process according to the invention for the preparation of nucleic acid from natural sources, the sources containing nucleic acids are first lysed. The lysate is left to rest for some time. Preferably, the resting time is at least 1 minute, from 5 to 10 minutes being particularly preferred. The resulting lysate then passes a filter layer of glass, silica gel, titanium oxide, aluminium oxide or packed diatomaceous earth, or interwoven or cemented non-wovens of glass fibers and silica gel, as well as cellulose, paper, compressed paper, paper non-wovens. Thereafter, the fraction leaving the filter layer is collected and the nucleic acid is subsequently isolated and purified from the collected fraction.

Especially with a packed filter layer of silica gel having a particle size of from 15 to 30 $\mu$m, cell fragments can be retained successfully and without any clogging of the filter, and a clear lysate can be obtained.

Preferably, the filter layers are modified such that there is no affinity for nucleic acids. In particular, minerals bearing hydroxy groups or coated materials, such as diol-silica gel, diol-diatomaceous earth, and/or diol-perlite, may be used.

In a preferred embodiment, sample flow through the filter layer may be facilitated by applying positive or negative pressure. However, due to the pore size configuration of the filter layer, passage of the sample to be filtrated through the filter layer is also possible driven by gravity. Furthermore, in order to accelerate the passage of sample through the filter layer, the sample may also be passed through the filter layer by centrifugation.

As the filter layers, there are used, e.g., silica gel, glass or diatomaceous earth having particle sizes of from 5 $\mu$m to 100 $\mu$m.

A particularly preferred filter layer is untreated diatomaceous earth or modified diol-diatomaceous earth having flow values of from 0.1 to 15 Darcy.

The sources containing nucleic acids may be cells from cell cultures, any kind of tissues, body fluids or microorganisms.

The process according to the invention is particularly suitable for the preparation of plasmid DNA from *E. coli*, yeast or eukaryontic cells, or of genomic DNA from blood or cells, the DNA having a size of from 1 to 50 kb. The process according to the invention is also useful for purifying plasmid DNA, cosmid DNA, in particular for molecular-biological research, such as cloning and sequencing, plasmid DNA for gene therapy, genomic DNA for analytics, diagnostics and gene therapy, and/or viral nucleic acids.

The positive pressure at the side before the passage through the filter layer is preferably achieved by means of a piston.

Preferably, the filtration is followed by further processing steps, such as separation on anion exchangers and/or adsorption to and desorption from other mineral supports.

A device for performing the process consists of a hollow body in which the filter layer is arranged. The filter layer is preferably arranged between two fixing means. As said hollow body, there may be used a syringe, in particular.

As the filter layer which may be used in the process according to the invention, there may be used layers in the form of packings, in particular of glass, silica gel, titanium oxide, alumina, or diatomaceous earth, e.g. cellite or silica gel or perlite, but also interwoven or cemented non-wovens of glass fibers and silica, as well as paper, compressed paper, paper non-wovens, or combinations thereof. Other particles suitable for filtration made of minerals or synthetic polymers, diatomaceous earth, silica gel, perlite, and other mineral supports are either untreated or treated to have a hydrophilic surface which is hardly capable of adsorbing nucleic acids, e.g. diol modified diatomaceous earth.

In a preferred embodiment of the process according to the invention, multiple samples are processed simultaneously and passed through appropriate devices advantageously adapted to microtitration systems.

A suitable device for performing the process according to the invention consists of a preferably cylindrical hollow body having an inlet and outlet and a filtration means arranged in the hollow body. For securing the filtration means, common securing means may be used, such as, for example, cementings, but also securing by frictional forces by jamming the filtration means in the hollow body.

BRIEF DESCRIPTION OF THE DRAWING

The device consists of at least one filter layer with equal pore sizes as seen in the direction of outlet 60. FIG. 1 shows a particularly preferred variant of the device, where in the preferably cylindrical hollow body 40, the filtration means 70 is designed from one sheet. The particle size of the filter layer is in the range of from 5 µm to 500 µm at a total thickness of the filter layer of from 0.1 to 200 mm.

It may be advantageous to arrange an additional layer 23 in the hollow body 40, namely, above and/or below layer 20, which prevents premature penetration of the solution to be filtered into the filter, or leaking of the solution from the device according to the invention.

However, it is also possible to design layer 20 as a porous, hydrophobic layer. Where the hydrophobic separating layer 23 is arranged above separating layer 20, it is advantageous if the pore size of this separating layer is not smaller than that of underlying layer 20. With the other configuration, where the hydrophobic separating layer is arranged beneath layer 20, this requirement is less critical.

Preferably, the device has a piston 80, by means of which a pressure can be build in the hollow body 40 whereby the passage of the sample through layer 20 is promoted.

In another preferred embodiment, the device according to the invention is capable of being combined with other instruments necessary for the preparation of nucleic acids, as disclosed, e.g., in P 41 39 664.

P 41 27 276 discloses anion exchangers which are embedded in a membrane (3M Empore Membrane). Such systems are commercially available under the designation of QIAwell®.

EXAMPLE 1
Synthesis of Diol-Diatomaceous Earth 100 g of diatomaceous earth is mixed with 2,000 ml of 10% glymo (g-glycidooxypropyltrimethoxysilane) in toluene or carbon tetrachloride and degassed and refluxed for 6 hours.

The epoxy-diatomaceous earth produced is collected by sucking and washed with toluene and subsequently with methanol and water.

For the preparation of the diol form, the epoxy-diatomaceous earth is refluxed with 10 mM $H_2SO_4$/water for 3 h.

The diol-diatomaceous earth produced is thoroughly washed with water and dried.

The dried diol-diatomaceous earth is directly employed for filtration. The diol-diatomaceous earth may also be synthesized according to other synthesis protocols such as those described in the literature.

EXAMPLE 2
Filter for Fermenter Cultures

A chromatographic column of about 2,000 ml (10 cm×25 cm) is closed at its lower end with an appropriate 50 µm PE frit or a nylon net and filled with diol-diatomaceous earth to a height of 5 cm. The diol-diatomaceous earth is covered with a very coarse filter cloth (ca. 150 to 200 µm). Two liters of *E. coli* cell lysate (prepared from the lysis of 1 vol. of *E. coli* cells in TE with 1 vol. of 0.1 M NaOH/1% SDS, and neutralisation with 1 vol. of 3 M potassium acetate, pH 4.5) is filled into the filter column and allowed to rest for 15 min. The filtrate is pumped off through the lower column opening by means of a peristaltic pump and directly passed through a anion-exchange chromatographic column with DEAE-Sepharose FF (Pharmacia).

EXAMPLE 3

A 15 ml disposable syringe (diameter: 1.5×15 cm) is closed at its lower end with a porous 50 µm PE frit and filled with 15 to 25 µm of silica gel to a height of 1 cm and again closed at its upper end with a 50 µm frit according to FIG. 1. A 100 ml *E. coli* cell culture is centrifuged and resuspended in 5 ml of TE buffer (10 mM Tris, 1 mM EDTA, pH 7.5) and lysed by the addition of 1 vol. of 0.1 M NaOH/1% SDS. The cell lysis is stopped by the addition of 1 vol. of 3 M potassium acetate, pH 4.8, and the cell lysate including the precipitated proteins, K-dodecyl sulfate, genomic DNA and cell fragments is filled in the filter column. The cell lysate rests for 10 min wherein the lighter cell fragments, proteins and the precipitated KDS rise to the top. Such incubation prevents premature clogging of the filter layer with the cell fragments and thus increases the soil uptake and retaining capacity of the filter layer by several times its value. The filtrate is pressed through the silica gel layer with a piston. Subsequently, the clear lysate can immediately be subjected to a further nucleic acid purification by anion exchange chromatography, gel filtration or precipitation with alcohol.

The filter layer with the cell fragments is discarded.

What is claimed is:

1. A filtration process for the preparation of plasmid-DNA from a microorganism, the plasmid-DNA being suitable for gene therapy, the process comprising the steps of:
    (a) lysing the microorganism, thereby effecting a lysate;
    (b) allowing the lysate to rest for at least one minute;
    (c) passing the resulting lysate through a filter layer of packed diatomaceous earth that has not been modified with anion exchange groups, having a particle size between 5 µm and 500 µm; and
    (d) collecting the fraction which elutes from the packed diatomaceous earth, optionally followed by isolating the plasmid-DNA from the collected fraction.

2. The process according to claim 1, wherein the diatomaceous earth is modified to have no affinity for nucleic acids.

3. The process according to claim 2, wherein the diatomaceous earth is modified with minerals bearing hydroxy groups.

4. The process according to claim 3, wherein the minerals are diol silica gel, diol-diatomaceous earth, and/or diol-perlite.

5. The process according to claim 4, wherein the minerals arc diol-diatomaceous earth.

6. The process according to claim 1, wherein passing the lysate through the diatomaceous earth is facilitated by applying a positive pressure on the side of the diatomaceous earth before the passage or a negative pressure on the side of the diatomaceous earth after the passage.

7. The process according to claim 1, wherein said diatomaceous earth consists of untreated diatomaceous earth or diol-diatomaceous earth having flow values of from 0.1 to 15 Darcy.

8. The process according to claim 1, wherein said diatomaceous earth is arranged in a hollow body.

9. The process according to claim 1, wherein said diatomaceous earth is arranged in a hollow body between two fixing means.

10. The process according to claim 1, wherein said diatomaceous earth is arranged in a syringe body between two porous means.

11. The process according to claim 10, wherein said porous means are glass or plastic frits.

12. The process according to claim 6, wherein said positive pressure is applied by means of a piston.

13. A kit for perfoiming the process according to claim 1 comprising:

(a) a device containing the diatomaceous earth and (b) buffers required for performing the process.

14. The kit according to claim 13, wherein said device is a disposable syringe.

15. The kit according to claim 14, further comprising anion-exchange columns containing filters for the preparation of plasmid-DNA and/or cosmid-DNA.

* * * * *